(12) United States Patent
Fallat

(10) Patent No.: US 7,250,046 B1
(45) Date of Patent: Jul. 31, 2007

(54) TREATMENT OF LOWER EXTREMITY PAIN

(76) Inventor: Lawrence M. Fallat, 47461 Glengarry Blvd., Canton, MI (US) 48188

( * ) Notice: Subject to any disclaimer, the term of this patent is extended or adjusted under 35 U.S.C. 154(b) by 161 days.

(21) Appl. No.: 10/374,519

(22) Filed: Feb. 25, 2003

Related U.S. Application Data

(60) Provisional application No. 60/359,861, filed on Feb. 27, 2002.

(51) Int. Cl.
*A61B 18/18* (2006.01)
*A61B 19/00* (2006.01)
(52) U.S. Cl. .......................... 606/20; 128/898
(58) Field of Classification Search ............ 606/20–26; 607/11–113; 128/898
See application file for complete search history.

(56) References Cited

U.S. PATENT DOCUMENTS 6,190,378 B1 * 2/2001 Jarvinen ....................... 606/21

2005/0177215 A1 * 8/2005 Rosenberg .................. 307/111

OTHER PUBLICATIONS

"Cryogenic Denervation of the Intermetatarsal Space Neuroma" The Journal of Foot and Ankle Surgery, vol. 36, No. 4, 1997, Lawrence Hodor, Kevin Barkal, Lisa D. Hatch-Fox—pp. 311-314.

* cited by examiner

*Primary Examiner*—Michael Peffley
(74) *Attorney, Agent, or Firm*—Gifford, Krass, Sprinkle, Anderson & Citkowski, P.C.

(57) ABSTRACT

A method of treatment of lower extremity body pain is described comprising freezing a portion of the lower extremity, for example, for cryoanalgesia. In one form, a method of treating a Morton's neuroma comprises freezing the neuroma in the foot. In another preferred form, a method of treating plantar fasciitis comprises freezing a tissue portion in or adjacent to the foot. The methods include inserting a cryogenic probe through a skin surface for percutaneous access to a region for cryoanalgesia, and operating the probe to provide one or more successive freeze cycles.

11 Claims, 4 Drawing Sheets

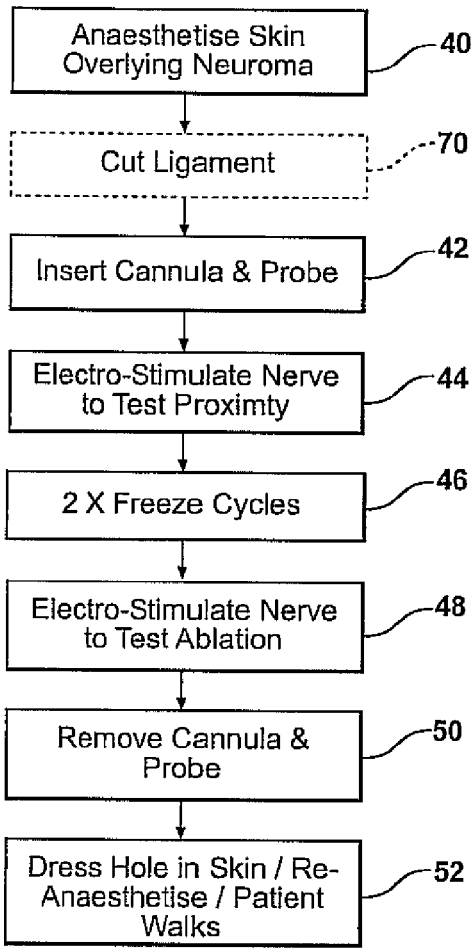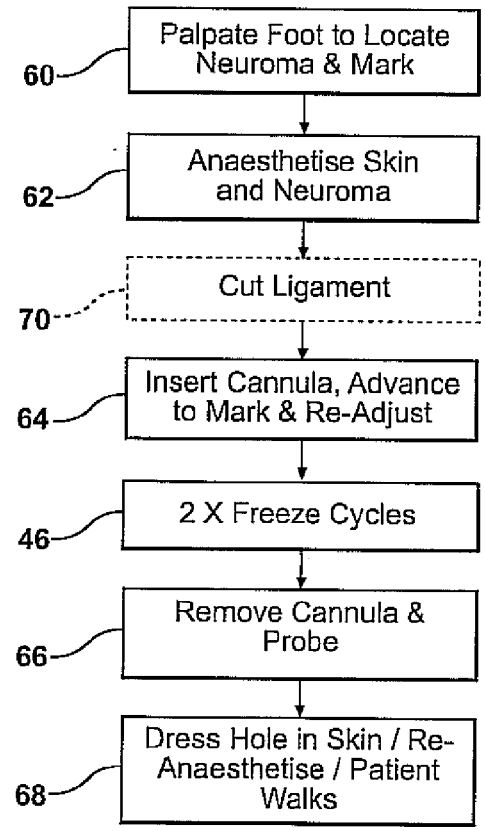

TREATMENT OF LOWER EXTREMITY PAIN

This application claims the benefit of U.S. Provisional Application No. 60/359,861, filed Feb. 27, 2002 and is hereby incorporated by reference in its entirety.

FIELD OF THE INVENTION

The present invention may relate to the treatment of pain in the human body lower extremity. The invention may be especially, but not exclusively, suitable for the treatment of neuromas (for example Morton's neuroma) and plantar fasciitis.

BACKGROUND TO THE INVENTION

A neuroma is a progressive degenerative enlargement of a nerve that is often associated with severe lancinating pain and cramping. Neuroma pain can become debilitating, limiting patients' physical activities in daily life, and severely limiting their quality of life. In extreme cases, patients may be forced to use crutches to move about. Neuroma formation in the lower extremity is one of the most common causes of foot and ankle pain encountered by foot and ankle surgeons.

It is estimated that up to 8 million people in North America may suffer from a Morton's neuroma. A Morton's neuroma is a neuroma created in the foot, between the bones of adjacent toes, most commonly between the third and fourth toes, but also commonly between the second and third toes. The neuroma can be caused by bones rubbing together repeatedly around the nerve, or by abrasion of the nerve by the ligament.

Current treatments for Morton's neuroma include:

(a) Accommodative orthotics (custom shoe inserts) for adjusting the structural support for the foot to reduce nerve irritation. The effect of such treatment is relatively modest;

(b) Pain relief injections, for example, non-steroidal anti-inflammatories and corticosteroid injections. These can be more effective than accommodative orthotics, but the effectiveness may be reduced by repeated injections, and injections are commonly ineffective for severe neuromas;

(c) Surgical excision of the neuroma. This requires an invasive surgical procedure, supervised by an anaesthetist, and involving the risks associated with any surgery. The treatment is relatively expensive, and is normally reserved for patients who fail to respond to the foregoing treatments. After the procedure, the patient is disabled during recovery for a period of three to six weeks. Moreover, the failure rate of surgical neurectomies exceeds 20%. It is not uncommon for a neuroma (a traumatic amputation or "stump" neuroma) to reoccur at the point of excision of the inciting neuroma. Such a recurring neuroma often has the same or worse debilitating pain symptomatology as the inciting neuroma, and may require further surgery.

Another common, and painful, foot problem is plantar fasciitis, caused by deterioration of the plantar fascia in the foot. It is estimated that up to 40 million people may be affected by such a problem.

SUMMARY OF THE INVENTION

The invention may provide a method of treatment of lower extremity pain in a lower extremity of the body. The method may comprise freezing a portion of the lower extremity.

Advantages of the invention may include one or more of: providing an alternative to invasive surgery for treating lower extremity pain; avoiding the risks, expense and inconvenience of surgery; providing faster recovery than possible following surgery; avoiding causes of surgical complication; and/or avoiding surface trauma to the nerve, and therefore reducing the likelihood of a traumatic amputation neuroma occurring at the point of the inciting neuroma.

Further features, objects and advantages will become apparent from the following description, the appended claims and drawings.

BRIEF DESCRIPTION OF THE DRAWINGS

Non-limiting embodiments of the invention are now described, by way of example, with reference to the claims and the accompanying drawings, in which;

FIG. 4 is a schematic flow diagram of the steps of a procedure for treating the neuroma in a first embodiment.

FIG. 5 is a schematic flow diagram of the steps of a procedure for treating the neuroma in a second embodiment.

DETAILED DESCRIPTION OF PREFERRED EMBODIMENTS

The following embodiments may illustrate the treatment of lower extremity pain by freezing a portion of the lower extremity. The freezing may produce cryoanalgesia. The freezing may be effective to partly or wholly desensitize nerve tissue at, or in a region adjacent to, a site of pain, and may also be referred to as partial or whole denervation (or cryoablation). The nerve may remain in situ. The freezing may deaden, destroy, or kill nerve tissue.

The term "lower extremity" may refer to parts of the body below the hip. For example, the term "lower extremity" may optionally refer to from the knee down, or optionally refer to below the knee, or optionally refer to the ankle and foot.

Figure 1:
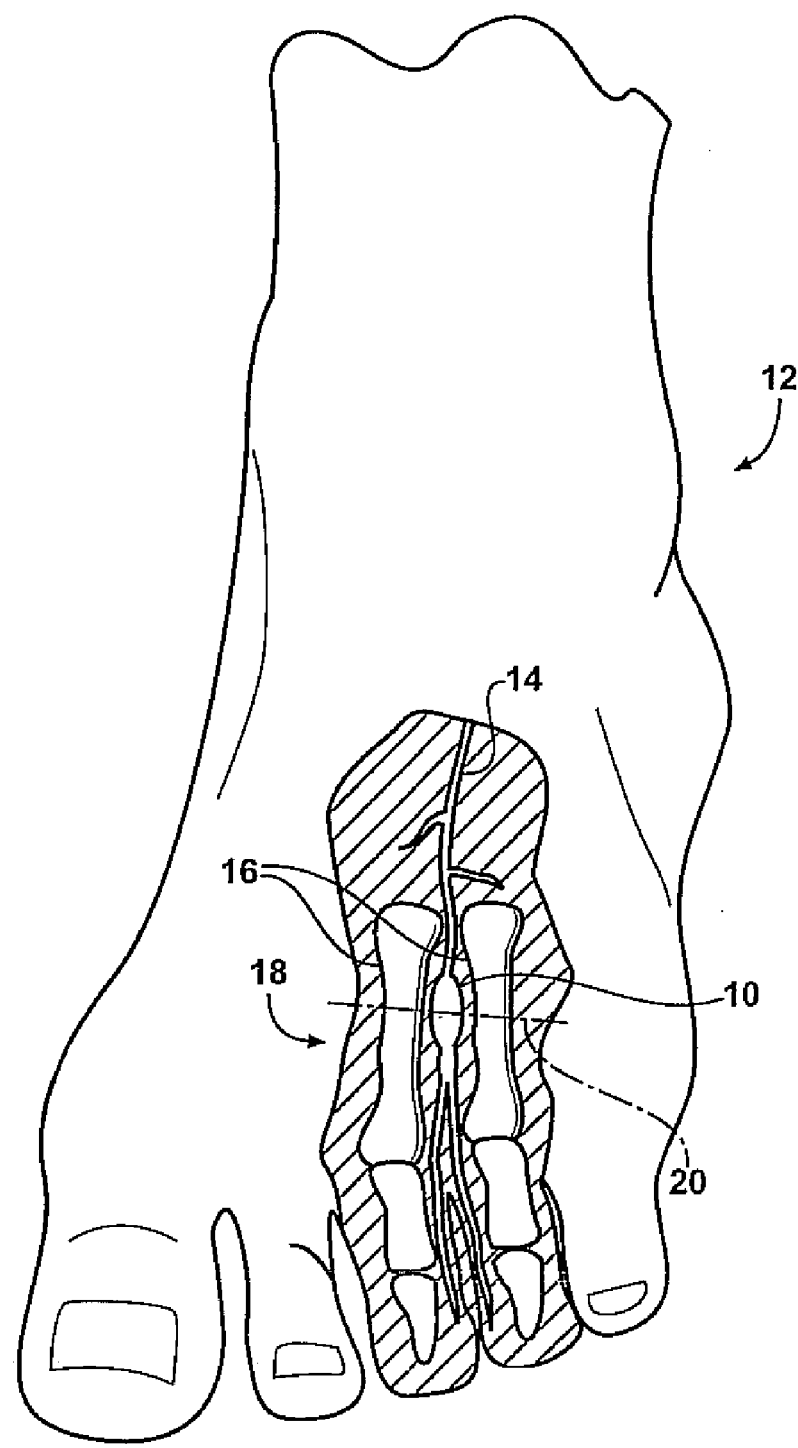
FIG. 1 is a schematic perspective view of a human foot showing the location of a Morton's neuroma.
Figure 2:
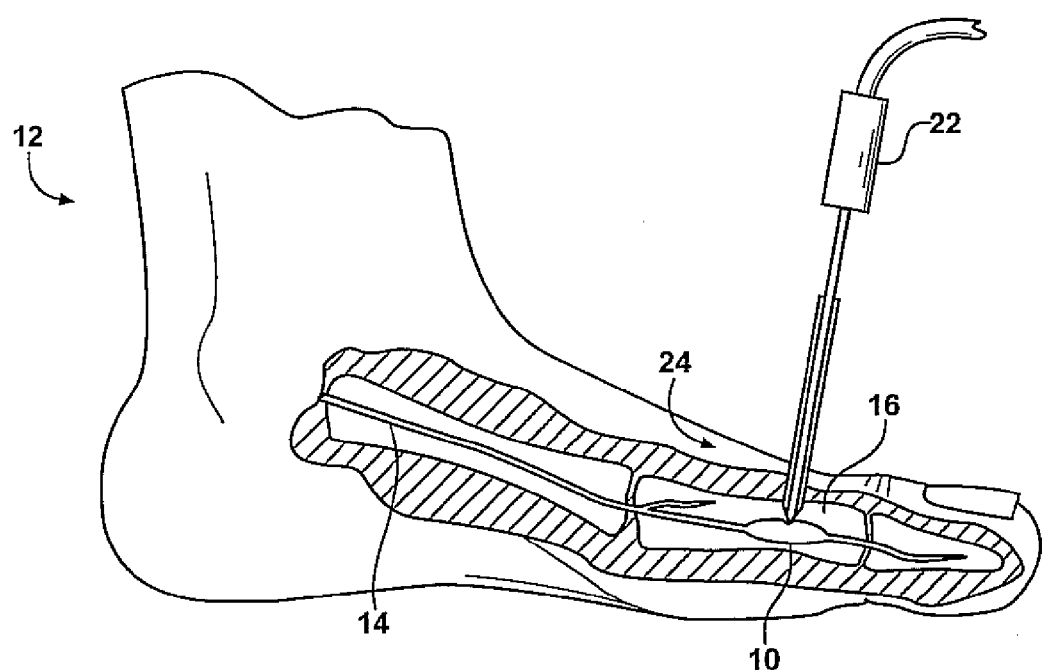
FIG. 2 is a schematic side view showing the locating of a cryogenic probe for cryoanalgesia of the neuroma.

Referring to FIGS. 1 and 2, one application of the invention may be a treatment of a neuroma (also called a Morton's neuroma) 10 which can occur in the foot 12, on a peripheral nerve 14 between the bones 16 of two toes. The neuroma 10 may be located towards the underside of the foot, adjacent to bone joints 18 and to a transverse Metatarsal ligament 20.

The treatment may involve percutaneous cryoanalgesia of the nerve 14 and its neuroma 10. A cryogenic probe 22 may be inserted into the foot 12. The freezing effect may be generated at a tip 24 of the probe 22, which may preferably be positioned to be adjacent to the neuroma 10. Various methods for positioning the probe 22 are described below in relation to specific procedure embodiments. Appropriate positioning of the probe is desirable, in order to optimise freezing of the neuroma. Misalignment of the probe 22 may not cause other critical tissue damage. However, the effectiveness of the treatment might be reduced if regions of the neuroma remain unfrozen. Although the probe 22 is shown as being inserted perpendicularly in FIG. 2, the probe may be inclined as desired to reach the neuroma 10.

Figure 3:
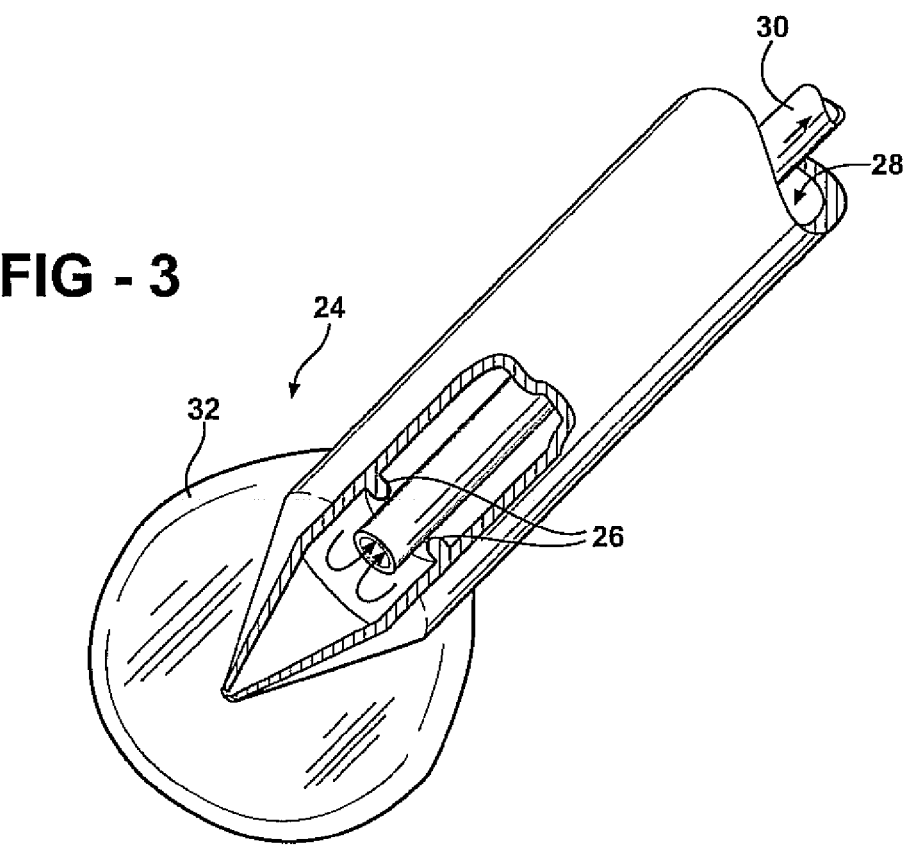
FIG. 3 is a schematic, cut-away perspective view showing the operating principle of the cryogenic probe.

Cryogenic probes 22 and their refrigerant engines (not shown) may be known per se. For example, the probe 22 may be a Westco Neurostat-III Cryoneedle produced by Westco Medical Corporation, San Diego, Calif. Referring to FIG. 3, the probe tip 24 may include an internal annular constriction 26 through which a gas may be forced under pressure. The gas may be supplied to, and exhausted from, the tip 24 by internal inlet and outlet passages 28 and 30, respectively. The expansion of the gas throttled by the constriction 26 may generate a substantial cooling effect, sufficient to lower the temperature at the tip to significantly below freezing. For example, using nitrous oxide gas, temperatures of about—70 degrees Celsius may be achieved. In use, an ice-ball 32 may be created within the body tissue, centered around the probe tip 24. Using the above-mentioned probe, the ice-ball diameter may typically be about 5.5 mm. The ice-ball size may depend on one or more of the size of probe used, the refrigerant gas, and the controller for the probe.

The ice-ball 32 may deaden, kill or destroy nerve tissue within the neuroma 10, and cause extensive vascular damage to the endoneurial capillaries or vas nervorum. This in turn may initiate demyelinization and subsequent Wallerian degeneration of the axon. The perineurium and epineurium may nevertheless be preserved, thereby preserving a basic architecture of the nerve. Such preservation may provide an important advantage of the cryogenic procedure in that it may avoid the occurrence of an amputation neuroma at the treatment site. As explained previously, an amputation neuroma is a common complication when a surgical extraction of the original neuroma is performed, due to the nerve trauma. Such an amputation neuroma can often be as debilitating, if not worse, than the original neuroma.

It is preferred that the freezing may be performed a plurality of times during the same procedure, although a single freeze cycle may be performed. In the following examples, two freeze cycles are used, although it will be appreciated that a greater number of freeze cycles may be used as desired or as required. In the present techniques, the duration of at least one (continuous) freeze cycle may be at least 1 minute, or at least 2 minutes, or at least 2.5 minutes, or at least 3 minutes, or at least 4 minutes, or at least 5 minutes, or at least 6 minutes, or longer. However, each freeze duration may be reduced to less than 1 minute if desired. In general, the use of repeated freeze cycles and/or relatively lengthy freeze durations, may increase the thoroughness and extent to which the neuroma may be frozen and, consequently denervated. It may be preferred that the duration of a continuous freeze cycle be longer than 2 minutes, for optimum freezing.

In some cases, it may be preferred to limit the number of freeze cycles performed with the probe 22 maintained in the same position. Each time a freeze cycle is performed, more tissue may be affected. Although cryoanalgesia may generally preserve the nerve perineurium and/or epineurium (as explained above), too many freeze cycles at the same position may risk destruction of, or damage to, the nerve perineurium and/or epineurium, leading to a risk of an amputation neuroma if these structures are damaged. In one non-limiting example, no more than two consecutive freeze cycles may be performed without moving the probe 22. For example, the probe 22 may be moved slightly proximal or distal to the neuroma. The probe 22 may be repositioned without removing the probe 22 from the skin. Such repositioning may be a minor adjustment to increase an area of the neuroma targeted by the cryoanalgesia. During repositioning of the probe, it may be preferred to limit the distance moved to less than the diameter of the ice-ball 32. Limiting the distance moved in this way may provide a continuous area of targeted tissue.

It may be preferred to insert the probe 22 from the upper (e.g., dorsal) side of the foot, in order to avoid puncturing the underside (e.g., sole or plantar) of the foot. Insertion from above may be counterintuitive, because the neuroma may be closer to the sole than to the dorsal surface. Insertion of the probe 22 from above may involve passing the probe through more tissue than if the probe 22 is inserted through the sole. However, in devising the present invention, it has been appreciated that the underside skin may be relatively thick and may take longer to heal. Moreover, if the sole is punctured, then the patient may not be able to walk immediately after the procedure. In contrast, by inserting the probe 22 from above, the sole can remain intact, and the patient may be able to walk on the treated foot much sooner. However, the probe 22 may nevertheless be inserted from below the foot, for example, to target regions of a large neuroma which might otherwise be difficult to reach from above.

FIG. 4 may illustrate the steps of a first embodiment of the treatment. A first step 40 may be to anaesthetize the skin on the upper surface of the foot overlying the region of the neuroma. For example, anaesthesia may be achieved by subcutaneous injection of approximately 0.5 cc of xylocalne. In this first embodiment, it may be desirable to avoid anaesthetising the underlying neuroma. At step 42, a cannula (e.g., 12 gauge) may be passed percutaneously through the anaesthetized skin into the vicinity of the symptomatic nerve. Such a cannula is not essential in all embodiments, but may be preferred to provide a degree of thermal protection for tissue around the neuroma. For example, if the neuroma is close to the skin surface, then the cannula may be useful to avoid, or at least limit, the extent to which the skin itself might be frozen. At step 44, a nerve stimulator, located in the tip 24 of the cryogenic probe 22 (e.g., a conductive surface of the tip 24) may be activated to elicit a pain response from the patient. A sharp pain response may indicate that the tip 24 of the probe 22 is located close to the neuroma. Several short activations may be used to enable the probe to be positioned accurately as close to the neuroma as possible.

At step 46, the probe may be operated to provide two sequential freeze cycles. Each freeze cycle may be about 3 minutes in duration. The thaw cycle may be of about 30 seconds. The probe may be moved between freeze cycles, or the probe may be left in the same position. For example, the probe may be moved slightly proximal or distal to the neuroma. Such repositioning may be a minor adjustment to increase the area of the neuroma targeted by cryoanalgesia. In one example, the probe is operated for no more than two freeze cycles in the same position.

At step 48, the nerve stimulator may again be activated to determine if there remains any residual pain. If the patient detects pain, then the procedure may be repeated from step 46. If the pain cannot be completely removed after the repetition, or if it is known that the neuroma 10 is larger than the size of ice-ball 32, then the probe 22 may be repositioned (after thawing) at a new location to target a different area of the neuroma. The procedure may be repeated at the new location. The new location may be on an opposite side of the foot to the first insertion.

At step 50, the probe 22 may be removed after thawing, and at step 52 the operative site may be sealed or covered. For example, a dry sterile dressing may be applied to the operative site.

The above procedure may allow the probe 22 to be positioned accurately for optimum freezing of the neuroma, by relying on the pain response of the patient to nerve stimulation. In certain cases, it might be beneficial to provide an alternative procedure which may be less painful for the patient, for optimizing patient comfort and patient acceptance of the procedure.

FIG. 5 may illustrate the steps of an alternative second embodiment of the procedure. Where appropriate, the same reference numerals may be used to denote steps in common with the first embodiment. Referring to FIG. 5, a first step 60 may be to locate the position of the neuroma by palpating the foot from below. The patient may feel the palpating pressure when applied to the neuroma, and identify when the neuroma is palpated. The position may be marked on a first surface of the foot, for example, the underside of the foot. A pen mark may be used to mark the position.

At step 62, the region of the foot containing the neuroma, including the overlying skin (for example, on a second surface, such as the upper surface) and the neuroma itself, may be anaesthetized. For example, 3-5 cc of xylocalne may be injected subcutaneously. By anaesthetizing the neuroma, the patient may not be subjected to any further discomfort during the procedure.

At step 64, a cannula may be passed percutaneously through the anaesthetized skin to a location on the nerve just proximal to the neuroma. Such a cannula is not essential in all embodiments, but may be preferred to provide a degree of thermal protection for the same reasons as described previously. In more detail, in this second embodiment, the probe 22 may be positioned by steering the tip 24 from the second (e.g. upper) surface of the foot towards the mark made on the first (e.g., lower) surface. The probe 22 may be aimed just rearward of the mark, and may be advanced until the tip 24 creates a slight bulge in the skin surface just rearward of the pen mark. Thereafter, the probe 22 may be withdrawn a certain distance, for example, between ¼ and ⅛ inch, thereby positioning the probe tip 24 closely adjacent to the neuroma.

The process may then proceed through the freeze cycles of step 46 as described in the first embodiment. Thereafter, no nerve stimulation may be used, as the tissue may already be anaesthetized, and the patient might not have any pain response.

At step 66 the probe may be removed, and at step 68, a dressing may be applied to the surgical site. A further anaesthetic may be administered to the treatment region, for example, to reduce any post-treatment discomfort. A mix of phosphates and acetates may be preferred, for example, Celestone Soluspan, which is an equal mixture of both.

During the majority of the procedure, the treatment region may be anaesthetized, to avoid the patient suffering pain. The second embodiment may therefore provide a technique for positioning the probe sufficiently accurately for practical treatment, while prioritizing patient comfort. Patient comfort may be an important aspect for increasing patient acceptance of the procedure. The second embodiment may achieve just as good results as the first embodiment. A choice between the first and second embodiment procedures may depend on the practitioner's preferences, and/or on the patient's circumstances.

It may be envisaged that cryoanalgesia of lower extremity neuromas may be especially suitable for treating neuromas which would otherwise be candidates for surgical removal, when other less effective treatments (e.g., orthotics and pain relieving injections) have failed. However, compared to an invasive surgical procedure, cryoanalgesia may avoid the risks of invasive surgery, may avoid the need for a specialist anaesthetist, may avoid the common problem of an amputation neuroma, and/or may avoid a lengthy recovery period following the treatment. In many cases, particularly when the cryoprobe has been inserted only through the upper (dorsal) skin surface of the foot, the patient may walk immediately after the treatment (e.g., the same day), and may return to normal daily activities. The treatment may also be especially suitable for elderly patients, or patients with other medical conditions, who might be unsuitable for invasive surgery. A further advantage may be that the treatment can be carried out by any suitable physician, rather than involving the skills of an invasive surgeon.

Nerve tissue may be regenerative, and so the treated nerve may regrow as time passes after the procedure. Should the new nerve tissue include a neuroma, then a repeat treatment may be performed at some time in the future. However, since the treatment procedure may be relatively straightforward, a repeat treatment may be equally as straightforward.

In the first and second embodiments (FIGS. 4 and 5), an optional treatment step 70 may be illustrated prior to the cryoanalgesia. Optional step 70 may comprise cutting the Metatarsal ligament 20 between the Metatarsal bones 16. Depending on an individual case, or an individual practitioner, such a cutting step may be preferred in order to reduce the risk of reoccurrence of a neuroma. Cutting the Metatarsal ligament 20 may remove the ligament as a cause of nerve abrasion, and may also generally permit the bones 16 to spread further apart, which may reduce the risk of the bones rubbing against the nerve. It may be preferred that the cutting step be performed using the same hole in the skin as that for the cryoprobe and its cannula, in order to avoid creating a second opening. The opening may be enlarged slightly, if appropriate, to accommodate a larger cutting tool. Cutting the Metatarsal ligament 20 may be straightforward, and may not increase the treatment time significantly. A practitioner may prefer to cut the ligament 20 in all cases, as a pre-emptive measure to avoid problems which the ligament may cause if left uncut. Alternatively, a practitioner may prefer not to cut the ligament 20 for a patient's first treatment, but only if the patient is having a repeat treatment for a recurring neuroma. Whether or not the ligament should be cut may depend on the practitioner and/or the particular patient circumstances.

In FIGS. 4 and 5, the cutting step 70 may be shown as a specific step prior to insertion of the cryoprobe and cannula. However, the cutting step 70 may, if desired, be carried out at any suitable stage of the procedure. For example, in the first embodiment shown in FIG. 4, the cutting step 70 could instead follow step 44 or step 50. In the second embodiment shown in FIG. 5, the cutting step 70 could instead follow step 64, or step 66.

In the above embodiments, a single insertion of the cryogenic probe into the foot may be appropriate. However, in certain situations, more than one insertion may be called for. For example, if the patient has already undergone surgery for neuroma removal, and is now suffering from an amputation neuroma complication, then the amputation neuroma may be difficult to target by a single insertion. In such a case, it may be appropriate to use two probe insertions. One insertion may be through the top of the foot. Another insertion may through the underside. Such insertions may be carried out simultaneously using plural probes, or sequentially one after the other using a single probe. The probes may be positioned using the techniques of either the first or the second embodiments.

Figure 6:
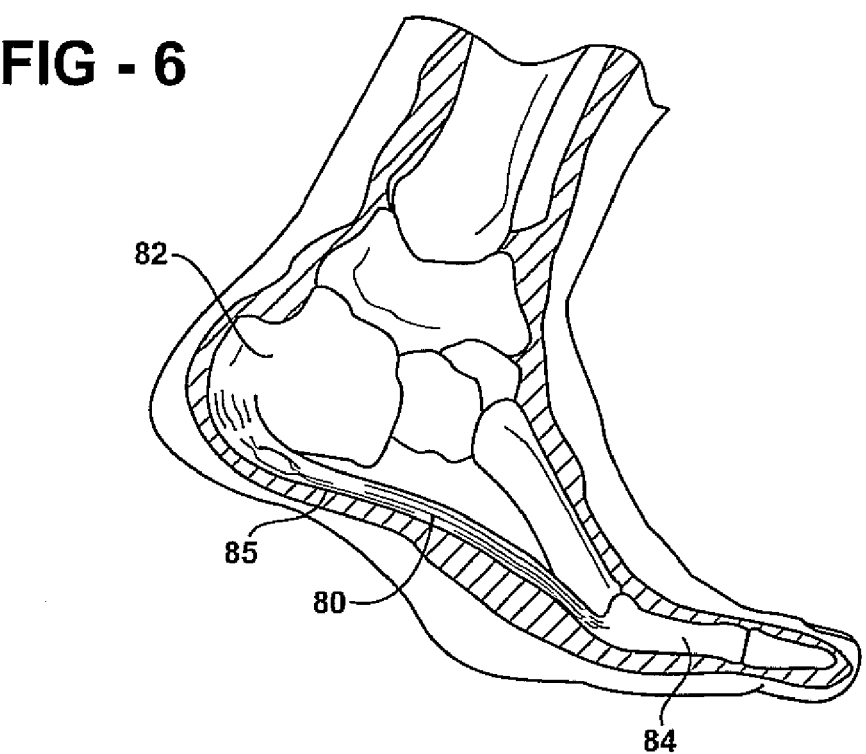
FIG. 6 is a schematic perspective view of a human foot showing the location of plantar fasciitis.
Figure 7:
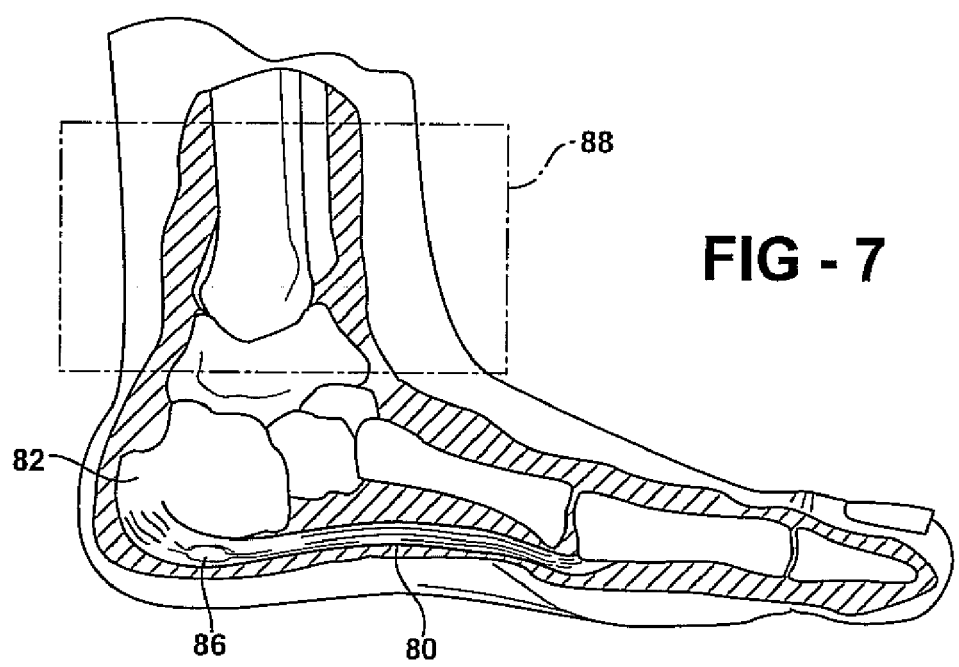
FIG. 7 is a schematic side view showing examples of the location of cryogenic probe sites for cryoanalgesia to treat plantar fasciitis.

Referring to FIGS. 6 and 7, a second application of the invention may be the pain treatment of plantar fasciitis. The plantar fascia 80 may be a ligament-like band running from the heal bone 82 to the ball 84 of the foot. The band 80 may pull on the heal bone, raising the arch of the foot as it pushes off the ground during walking. However, if the foot moves incorrectly, the plantar fascia can become strained, for example, at a point 85 close to the heel bone. The fascia may swell and its fibers may become inflamed, causing plantar fasciitis, similar to tendonitis.

Using procedures similar to either of the first and second embodiments, the pain may be treated in this second application of the invention by cryoanalgesia, for example, to partially or wholly denervate the painful region.

Referring to FIG. 7, in devising this application of the invention, it has been appreciated that several possible sites may be available for cryoanalgesia treatment. The choice of cryoanalgesia site may depend on the individual patient, the practitioner's preferences, and/or the ease of site and nerve location.

A first site 86 may be located below the ankle, adjacent to the point where the strain may occur in the plantar fascia, close to the heel bone 82. This site 86 may be accessed by inserting the cryoprobe 22 through the side of the foot adjacent to, but just below, the heel bone 82. Cryoanalgesia at this point 86 may be particularly effective for plantar fasciitis, as it may target the site of the pain. The painful region may be anaesthetized, for example, using 3-5 cc of an anaesthetic such as xylocaine. The cryogenic probe may be inserted at the target point, and the site maybe treated using one or more cryogenic freeze cycles, in a similar manner to that described previously.

A second site within a zone 88 may be located above the ankle, for targeting nerves exiting the foot. Cryoanalgesia at this point may likewise be particularly effective for plantar fasciitis, as it may target a major sensory nerve as it exits the foot.

As mentioned above, procedures similar to either the first or second embodiment may be used for the cryoanalgesia with only minor adaptation, and so such steps need not be described again in detail. The description of any of probe operation, length of freeze cycles, number of freeze cycles, and/or possible repositioning of the probe, may apply to cryoanalgesia for plantar fasciitis.

Some of the preferred techniques described herein may be summarized as:

(a) Optionally anaesthetize skin, but not a subcutaneous treatment site (for example, with 0.5 cc of an anaesthetic); stimulate nerve to position cryogenic probe; one or more freeze cycles.

(b) Palpate to locate sensitive treatment site; optionally anaesthetize skin and a subcutaneous treatment site (for example, with 3-5 cc of an anaesthetic); one or more freeze cycles.

(c) Inserting a cryogenic probe from above the foot.

(d) Using at least one freeze cycle of longer than 2 minutes, for example, at least 2 and a half minutes, or at least 3 minutes.

(e) Operating a cryogenic probe for no more than 2 freeze cycles in the same position of the probe.

(e) Making two or more probe insertions, for example, for treating large neuromas or in the case of previous surgery.

(f) Cutting the deep transverse Metatarsal ligament. For example, the ligament may be cut prior to cryoanalgesia.

(g) Optionally anaesthetize (for example, with 3-5 cc of an anaesthetic); position cryogenic probe (for example, with or without stimulation); one or more freeze cycles to freeze portion of nerve and/or portion of plantar fascia.

Other applications of the invention for the treatment of lower extremity pain will occur to the skilled man on reading the above, and the invention is to be construed broadly to cover all such applications. However, the invention may be particularly suitable and effective for the treatment of Morton's neuromas and plantar fasciitis, which remain highly preferred treatment applications.

The foregoing description is merely illustrative of preferred forms of the invention, and many modifications and equivalents may be used within the scope of the invention. Accordingly, the appended claims are intended to be broadly construed, and to include all such modifications and equivalents.

The invention claimed is:

1. A method for treating plantar fasciitis, said method comprising the steps of:
   providing a cryogenic probe;
   inserting said probe into the tissue of the lower leg and/or foot of a patient; and
   operating said probe so as to freeze a portion of said tissue.

2. The method of claim 1, wherein said probe is inserted into the tissue of said patient in a region adjacent to an ankle.

3. The method of claim 1, wherein said probe is inserted into the tissue of said patient in a region above an ankle.

4. The method of claim 1, wherein said probe is inserted into the tissue of a patient in a region below an ankle.

5. The method of claim 1, wherein said probe is inserted into the tissue of a patient in a region adjacent to a heel bone.

6. The method of claim 1, wherein said probe is inserted into at least a portion of a plantar fascia of said patient.

7. The method of claim 1, wherein said step of operating said probe so as to freeze said tissue comprises operating said probe in a first freeze cycle so as to freeze a portion of said tissue; allowing said frozen portion of tissue to thaw; and operating said probe in at least a second freeze cycle so as to refreeze said tissue which has been thawed.

8. The method of claim 1, wherein said probe is disposed so as to not penetrate the sole of said patient's foot.

9. The method of claim 1, wherein said probe is disposed so as to freeze at least a portion of a nerve.

10. The method of claim 1 including the further steps of:
    removing said probe from said patient;
    reinserting said probe into the tissue of the foot and/or the lower leg portion of said patient, in a region different from a region in which the probe was previously inserted; and
    operating said probe so as to freeze the tissue of said patient in said second region.

11. The method of claim 1, including the further step of anesthetizing a portion of the tissue of the foot and/or lower leg of said patient prior to the insertion of the probe thereinto.

\* \* \* \* \*